(12) United States Patent
Yamazaki et al.

(10) Patent No.: US 10,907,191 B2
(45) Date of Patent: Feb. 2, 2021

(54) METHOD FOR MEASURING ACTIVITY OF OXIDOREDUCTASE

(71) Applicant: NATIONAL AGRICULTURE AND FOOD RESEARCH ORGANIZATION, Tsukuba (JP)

(72) Inventors: Toshimasa Yamazaki, Tsukuba (JP); Yuki Nishigaya, Tsukuba (JP)

(73) Assignee: NATIONAL AGRICULTURE AND FOOD RESEARCH ORGANIZATION, Tsukuba (JP)

(*) Notice: Subject to any disclaimer, the term of this patent is extended or adjusted under 35 U.S.C. 154(b) by 130 days.

(21) Appl. No.: 16/071,821

(22) PCT Filed: Jan. 18, 2017

(86) PCT No.: PCT/JP2017/001522
§ 371 (c)(1),
(2) Date: Jul. 20, 2018

(87) PCT Pub. No.: WO2017/126542
PCT Pub. Date: Jul. 27, 2017

(65) Prior Publication Data
US 2019/0024138 A1    Jan. 24, 2019

(30) Foreign Application Priority Data
Jan. 22, 2016 (JP) ................... 2016-010983

(51) Int. Cl.
| | | |
|---|---|---|
| *C12Q 1/26* | (2006.01) | |
| *C12N 9/06* | (2006.01) | |
| *G01N 33/24* | (2006.01) | |
| *C12N 1/20* | (2006.01) | |
| *B01D 61/24* | (2006.01) | |
| *C12M 1/40* | (2006.01) | |
| *C12Q 1/02* | (2006.01) | |

(52) U.S. Cl.
CPC ............ *C12Q 1/26* (2013.01); *B01D 61/243* (2013.01); *C12M 21/18* (2013.01); *C12N 1/20* (2013.01); *C12N 9/0046* (2013.01); *C12Q 1/02* (2013.01); *C12Y 107/03004* (2013.01); *G01N 33/24* (2013.01)

(58) Field of Classification Search
CPC .... C12Q 1/26; C12Q 1/02; C12Y 107/03004; C12N 9/0046; C12N 1/20; G01N 33/24; B01D 61/243; C12M 21/18
See application file for complete search history.

(56) References Cited

U.S. PATENT DOCUMENTS 5,206,147 A * 4/1993 Hoenes ................ H05K 7/12
435/25

FOREIGN PATENT DOCUMENTS

JP    2-211899 A    8/1990

OTHER PUBLICATIONS

Jetten et al., Antonie van Leeuwenhoek, 1997, vol. 71, p. 69-74.*
O'Brien et al., FEBS, 2000, vol. 267, p. 5421-5426.*
International Search Report dated Apr. 11, 2017, in PCT/JP2017/001522 filed Jan. 18, 2017.
Schalk, J. et al., "Involvement of a Novel Hydroxylamine Oxidoreductase in Anaerobic Ammonium Oxidation", Biochemistry, vol. 39, 2000 pp. 5405-5412.
Nejidat, A. et al., "Effect of Ammonia Starvation on Hydroxylamine Oxidoreductase Activity of *Nitrosomonas europaea*", J. Biochem., vol. 121, 1997, pp. 957-960.
Shimamura, M. et al., "Another Multiheme Protein, Hydroxylamine Oxidoreductase, Abundantly Produced in an Anammox Bacterium Besides the Hydrazine-Oxidizing Enzyme", Journal of Bioscience and Bioengineering, vol. 105, No. 3, 2008, pp. 243-248.
Ewald, M. et al., "Short Term Test for the Determination of Dehydrogenase Activity of Activated Sludges", Von Wasser, vol. 68, 1987, pp. 165-175.
Nishigaya, Y. et al., "Structure based approach for nitrifiction inhibitor design targeting for hydroxylamine oxidoreductase", Proceedings of the Annual Meeting of Japan Society for Bioscience, Biotechnology and Agrochemistry, 2014, Lecture No. 4A07a09, 2 pages.
Nishigaya, Y. et al., "Kozo Kaiseki to Shinki Sogaizai o Riyo shita Ammonia Sanka Saikin Yurai no Hydroxylamine Sanka Kangen Koso ni Taisuru Shoka Yokuseizai Target to shiteno Validation", Annual Meeting of the Japanese Biochemical Society, 2P-097, 2014, 2 pages.
Maeda, H. et al., "Resazurin as an Electron Acceptor in Glucose Oxidase-Catalyzed Oxidation of Glucose", Chem. Pharm. Bull., vol. 49, No. 5, 2001, pp. 622-625.
Maalcke, W. J. et al., "Structural Basis of Biological NO Generation by Octaheme Oxidoreductases", The Journal of Biological Chemistry, vol. 289, No. 3, Jan. 17, 2014, pp. 1228-1242.

* cited by examiner

*Primary Examiner* — Kade Ariani
(74) *Attorney, Agent, or Firm* — Oblon, McClelland, Maier & Neustadt, L.L.P.

(57) ABSTRACT

The present invention relates to a method for measuring activity of HAO which comprises bringing HAO into contact with hydroxylamine in the presence of a tetrazolium salt. Further, the present invention also provides a method for culturing microorganisms which comprises culturing microorganisms in a storage container of a sample containing microorganisms installed separately in a liquid medium storage container, wherein the storage container of a sample containing microorganisms has pores.

5 Claims, 4 Drawing Sheets

Measurement of soil direct HAO activity applying resazurin method

Fluorescence-active staining of
native-PAGE applying resazurin method

METHOD FOR MEASURING ACTIVITY OF OXIDOREDUCTASE

TECHNICAL FIELD

The present invention relates to a method for measuring activity of hydroxylamine oxidoreductase (HAO) which comprises bringing HAO into contact with hydroxylamine in the presence of a tetrazolium salt. The present invention also relates to a method for producing HAO. The present invention further relates to a method for screening a HAO inhibitor which comprises bringing HAO into contact with hydroxylamine and a candidate compound in the presence of a tetrazolium salt. The present invention is further to provide a method for culturing microorganisms which comprises culturing microorganisms in a storage container of a sample containing microorganisms which are separately installed in a liquid culture storage container and the storage container of a sample containing microorganisms has a fine pore.

BACKGROUND ART

Nitrogen fertilizer, which is particularly important as chemical fertilizer, is overdosed on agricultural land as ammonia nitrogen ($NH_4^+$). However, most of the part thereof is nitrified, which causes runoff of the nitrogen fertilizer from agricultural land and formation of greenhouse gas ($N_2O$). Existing nitrification inhibitors involve the problems that they are volatile and cannot be used at temperatures of 20° C. or higher, have weak effects, have carcinogenicity and residual toxicity, and novel nitrification inhibitors are expected to solve these problems. The existing nitrification inhibitors are considered to be ammonia monooxygenase (AMO) as a target. On the other hand, nitrification inhibitors targeted to hydroxylamine oxidoreductase (Hydroxylamine oxidoreductase: HAO) which is a central enzyme of the nitrification reaction have not yet been known so far. Also, various methods for measuring the activity of HAO have been known, but none of them was satisfactory in terms of sensitivity and cost. Further, methods for measuring HAO activity that can be applied to high-throughput screening have not yet been developed so far.

Cultivation of microorganisms sometimes entails difficulties and the concentration of microbial cells at the time of culture is at most $OD_{600}=0.1$ (less than 1 g per 10 L), which requires not only a large amount of medium but also a lot of labor for collecting bacterial cells. This was a particularly serious problem in the case of microorganisms derived from a soil, a compost or an activated sludge.

PRIOR ART DOCUMENTS

Non-Patent Documents

Non-Patent document 1: H. Maeda, S. Matsu-ura, Y. Yamauchi, H. Ohmori, Resazurin as an electron acceptor in glucose oxidase-catalyzed oxidation of glucose., Chem. Pharm. Bull. 49 (2001) 622-625.

Non-Patent document 2: W. J. Maalcke, A. Dietl, S. J. Marritt, J. N. Butt, M. S. M. Jetten, J. T. Keltjens, T. R. M. Barends, B. Kartal, Structural basis of biological NO generation by octaheme oxidoreductases., J. Biol. Chem. 289 (2014) 1228-42.

Non-Patent document 3: J. Schalk, S. de Vries, J. G. Kuenen, M. S. Jetten, Involvement of a novel hydroxylamine oxidoreductase in anaerobic ammonium oxidation., Biochemistry. 39 (2000) 5405-12.

SUMMARY OF THE INVENTION

Problems to be Solved by the Invention

An object of the present invention is to provide a method for measuring activity of hydroxylamine oxidoreductase, which is practical in terms of sensitivity and cost, and which is convenient to measure. In addition, another object of the present invention is to provide a method for culturing microorganisms which can obtain a sufficiently satisfactory cell concentration while efficiently preparing a culture medium and collecting microbial cells in culturing microorganisms. It is further object of the present invention to provide a novel method capable of analyzing the activity of HAO conveniently, quickly and with high sensitivity from a sample containing a large number of enzymes.

Means to Solve the Problems

The present inventors have conducted extensive research, and as a result, they have found a method for measuring activity of a hydroxylamine oxidoreductase measured in a reaction system existing a large amount of hydroxylamine based on the tetrazolium salt, in particular, the resazurin salt of a tetrazolium salt, whereby they have completed the present invention. In addition, the present inventors have found that the presence or absence of the enzyme and the strength of the activity can be effectively analyzed by subjecting a sample containing nondenaturing HAO to gel electrophoresis, followed by enzymatic reaction in a gel, and by visualizing the reaction product by fluorescence measurement, whereby they have completed the invention of the present application.

That is, the gist of the present invention is as follows.

[1] A method for measuring activity of hydroxylamine oxidoreductase (HAO) which comprises bringing HAO into contact with hydroxylamine in the presence of a tetrazolium salt.

[2] The measurement method described in [1], wherein the tetrazolium salt is a resazurin salt.

[3] The measurement method described in [1] or [2], wherein the hydroxylamine is contacted with at a molar ratio of at least three times of the tetrazolium salt.

[4] The measurement method described in any one of [1] to [3], wherein the hydroxylamine is contacted with at a molar ratio of at least five times of the tetrazolium salt.

[5] The measurement method described in any one of [1] to [4], wherein the hydroxylamine is contacted with at a molar ratio of at least ten times of the tetrazolium salt.

[6] The measurement method described in any one of [1] to [5], wherein the measurement is carried out at a pH of 4.0 to 8.0.

[7] The measurement method described in any one of [1] to [6], wherein the measurement is carried out at a pH of 4.6 to 7.6.

[8] The measurement method described in any one of [1] to [7], wherein an object to be measured is a soil, a compost, an activated sludge or a polyacrylamide gel obtained by electrophoresing them in a nondenaturing state.

[9] A method for producing HAO which comprises purifying HAO from a sample containing HAO, and measuring activity of HAO by the measurement method described in any one of [1] to [8] to discriminate a fraction containing HAO in purification.

[10] The producing method described in [9], wherein the method contains drying purified HAO.

[11] A method for screening for HAO inhibitor which comprising bringing HAO into contact with hydroxylamine and a candidate compound in the presence of a tetrazolium salt.

[12] A method for culturing microorganisms which comprises culturing microorganisms in a storage container of a sample containing microorganisms installed separately in a liquid medium storage container, wherein the storage container of a sample containing microorganisms has pores.

[13] The culture method described in [12], wherein a volume ratio of the liquid medium and the sample containing microorganisms is from 10:1 to 1000:1.

[14] The culture method described in [12] or [13], wherein a molecular weight cut-off of the pores is 50 to 1,000 KDa.

[15] The culture method described in any one of [12] to [14], wherein the storage container of a sample containing microorganisms is a dialysis tube.

[16] The culture method described in any one of [12] to [15], wherein an enclosing port of the storage container of a sample containing microorganisms is sterilized.

[17] The culture method described in any one of [12] to [16], wherein the microorganism is a difficult-to-be-cultured microorganism.

[18] The culture method described in any one of [1] to [17], wherein the microorganism is a microorganism that reaches a stationary phase at a turbidity of $OD_{600}$ of 0.2 or less.

Effects of the Invention

According to the present invention, there is provided a method for measuring activity of HAO which can be carried out with a trace amount, high sensitivity, low price and homogeneous assay which has not been known in the prior art. The method for measuring the activity of HAO according to the present invention is suitable for high-throughput screening, can be directly detected from living bacteria, directly from a sample such as a soil, etc., or directly from a nondenaturing polyacrylamide electrophoresis gel. Measurement of the activity of HAO according to the present invention is possible even in the presence of usual oxygen, real-time measurement is also possible, and higher sensitivity can be obtained by fluorescence measurement. In the method for measuring the activity of HAO according to the present invention, an electron carrier such as PMS is not necessary. According to the present invention, it is also possible to effectively cultivate difficult-to-be-cultured microorganisms, particularly microorganisms in a soil, a compost or an activated sludge. In the method for producing HAO according to the present invention, ammonium sulfate fractionation is not carried out, so that the purification time is greatly shortened and scale-up becomes easy. HAO obtained by the present invention can be stored for a long time. When a culture solution containing ammonia oxidizing bacteria which has HAO, etc., is analyzed, the activity of HAO in the sample can be quantified. Further, when candidate compounds as HAO inhibitors to these samples are treated beforehand, the HAO inhibitory effect of the candidate compound can be conveniently analyzed.

EMBODIMENTS TO CARRY OUT THE INVENTION

Figure 1:
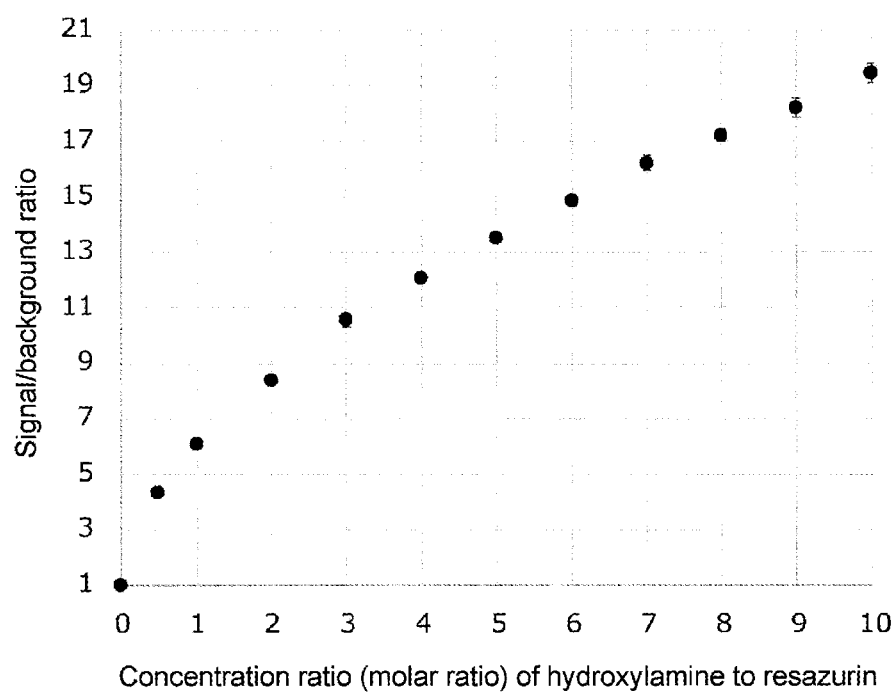
FIG. 1 shows the relationship in molar ratio of hydroxylamine to resazurin in the method for measuring HAO activity according to the present invention.
Figure 2:
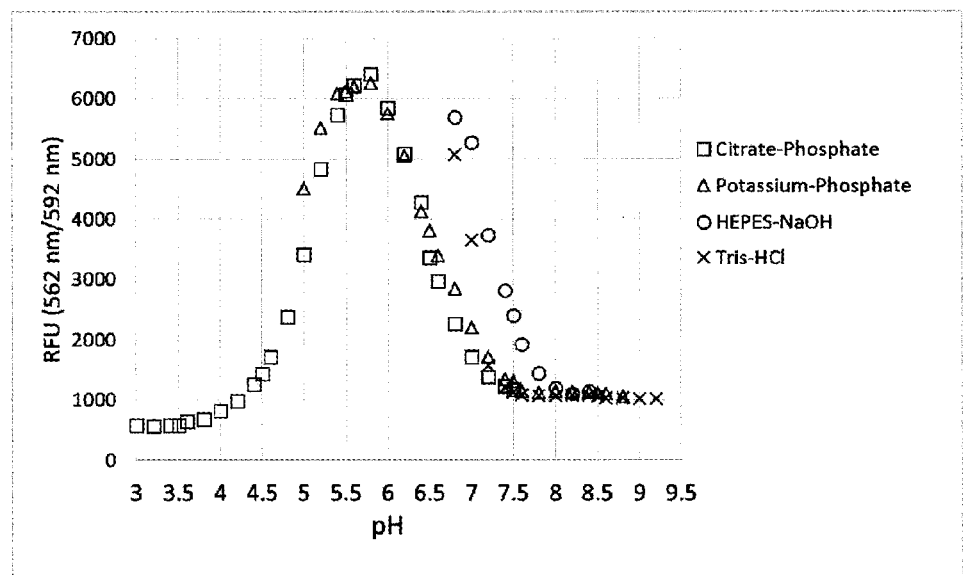
FIG. 2 shows pH dependency in the method for measuring HAO activity according to the present invention.
Figure 3:
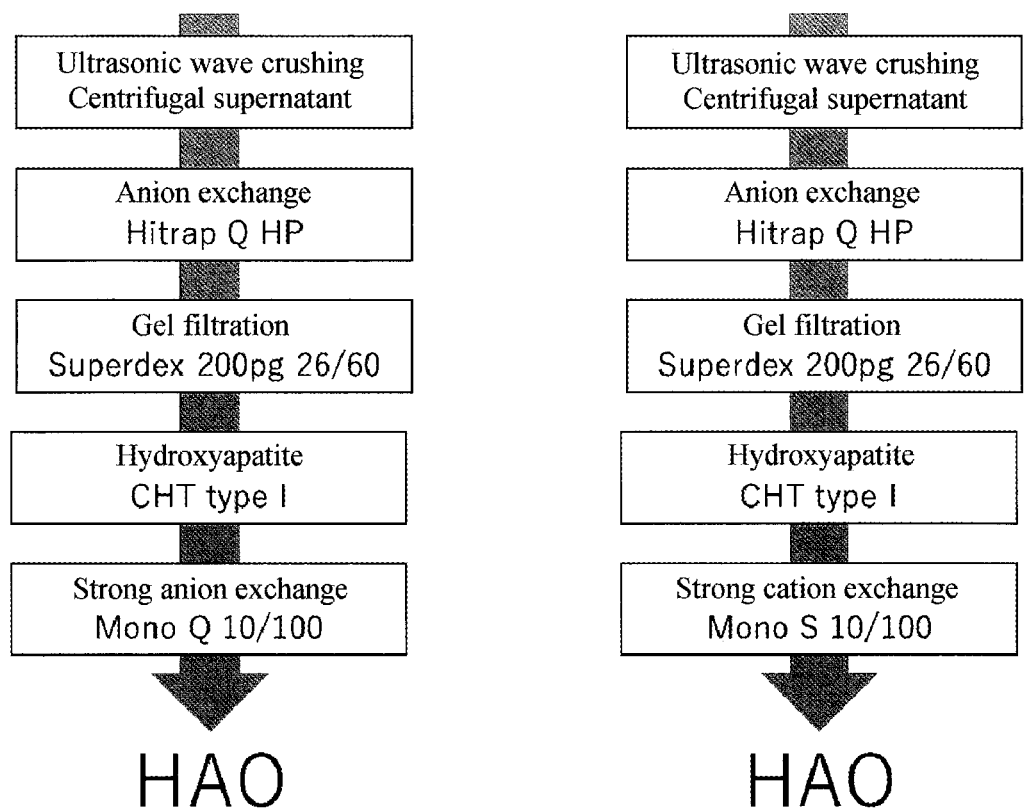
FIG. 3 shows an embodiment of the producing method of HAO according to the present invention.
Figure 4:
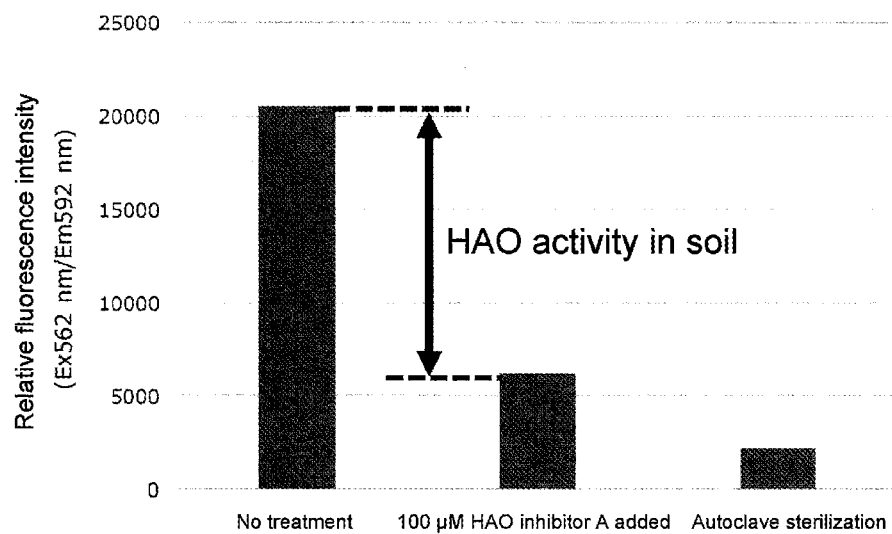
FIG. 4 shows an embodiment of the measurement of soil direct HAO activity according to the present invention.

The present invention is to provide a method for measuring activity of hydroxylamine oxidoreductase (HAO) which comprises bringing HAO into contact with hydroxylamine in the presence of a tetrazolium salt.

The method for measuring the activity of HAO of the present invention detects the change in the absorbance or the change to the fluorescent substance of the tetrazolium salt, preferably the resazurin salt of the tetrazolium salt.

In the method for measuring the activity of HAO of the present invention, the measurement is carried out in a reaction system in which hydroxylamine is present in an amount of at least 3 times, preferably 5 times, more preferably 10 times (molar ratio) with respect to a tetrazolium salt, preferably a resazurin salt.

In the method for measuring the activity of HAO of the present invention, it is preferable to measure at a pH from 4.0 to 8.0. It is preferable to measure at a pH from 4.6 to 7.6 since the signal background ratio becomes 2 or more. The buffer solution can be selected from a citrate-phosphate buffer solution, a potassium phosphate buffer solution, a HEPES-NaOH buffer solution, a Tris-HCl buffer solution, etc. When the buffer and the pH are changed, the HAO activity (initial velocity) changes, so that these conditions can be selected according to the purpose of the experiment. For example, the condition with the highest HAO activity reaching the maximum fluorescence intensity in about 15 minutes is suitable for rapid measurement or measurement when the HAO concentration is low. Therefore, it is a measurement condition suitable for a method requiring rapid measurement although strict quantification is not necessary such as confirmation of the HAO fraction at the time of HAO purification. As this condition, a potassium phosphate buffer solution and a citrate-phosphate buffer solution at a pH of about 5.6, a HEPES-NaOH buffer solution and a Tris-HCl buffer solution at a pH of about 6.8, etc., can be utilized. On the other hand, under relatively low HAO activity such that the maximum sensitivity is reached in about 2 to 3 hours, the incubation time error of several minutes can be neglected. For this reason, it becomes the measurement condition suitable for a method requiring a large number of assays be carried out in parallel, such as inhibitor screening, and suppression of fluctuation between assays. As this condition, a potassium phosphate buffer solution in the vicinity of a pH 7.0, etc., can be utilized.

In the method for measuring the activity of HAO of the present invention, the sample may be a solid matter or a liquid containing a bacterial community, preferably a soil, a compost or an activated sludge, and the activity of HAO contained therein may be directly measured. The activated sludge refers to sewage during the purification treatment including suspended sludge in which microorganisms abundantly exist, and means both sludge and sewage. The method for measuring the activity of the present invention enables fluorescent staining specifically for HAO from a large number of protein bands separated by nondenaturing polyacrylamide gel electrophoresis. In the nondenaturing polyacrylamide gel electrophoresis, HAO is separated while keeping activity in the gel. By bringing HAO in this gel into contact with hydroxylamine in the presence of a tetrazolium salt, the tetrazolium salt is changed to a fluorescent substance. Further, by using a gel imager light source and a filter for fluorescence observation, the fluorescent substance in the gel can be detected with high sensitivity. Thereby, blue light (440-500 nm) can be used as the excitation light source, more preferably cyan light (wavelength 480-530 nm), further preferably green light (490-580 nm) can be used. An orange filter can be used as a filter for fluorescence observation. As a method of the electrophoresis, native-PAGE, blue native-PAGE, etc., which are nondenaturing polyacrylamide gel electrophoresis methods can be utilized. As a sample to be subjected to electrophoresis, it may be a sample such as purified HAO, crushed supernatant of microbial cells, a soil sample, an activated sludge, etc., and a sample to which HAO inhibitor is added. When purified HAO in which a concentration or activity has been previously known is used as a marker, it is also possible to conveniently determine the HAO activity.

The method for measuring the activity of HAO of the present invention can be applied to high-throughput screening, and can screen inhibitors of HAO which is the central enzyme of nitrification reaction.

The present invention also provides a method for culturing microorganisms which comprises culturing the microorganisms in a storage container of a sample containing microorganisms installed separately in a liquid medium storage container, wherein the storage container of a sample containing microorganisms has pores.

In the method for culturing microorganisms according to the present invention, a volume ratio of the liquid medium and the sample containing microorganisms may be 10:1 to 1,000:1, preferably 100:1 to 800:1, more preferably 200:1 to 600:1, and most preferably 400:1.

In the method for culturing microorganisms according to the present invention, the liquid medium storage container may be a bottle of 1 to 50 L, preferably 3 to 30 L, more preferably 20 L, and it is not limited thereto, and it is characterized in that the method is easy in scale up the liquid medium storage container and scale up the storage container of a sample containing microorganisms. The storage container of a sample containing microorganisms may have any shape such as, for example, a cylinder, a tube, a dish, etc., and preferably a tube. The storage container of a sample containing microorganisms has pores, and the pores have a molecular weight cut-off (MWCO) of 50 KDa or more in order to make it difficult for growth suppression due to insufficient exchange of medium components to occur, and 1,000 KDa or less for not allowing microorganisms to pass therethrough. The storage container of a sample containing microorganisms is preferably a dialysis tube having such a fractionated molecular weight. An enclosing port of the storage container of a sample containing microorganisms is preferably sterilized.

In the method of culturing microorganisms according to the present invention, it is possible to culture difficult-to-be-cultured microorganisms as described in Journal of Environmental Biotechnology, Vol. 7, No. 2, 69-73, 2007, more specifically, difficult-to-be-cultured microorganisms reaching stationary phase at the cell number level of extremely low turbidity ($OD_{600}$ is 0.2 or less). Such microorganisms are, for example, ammonia oxidizing bacteria, ammonia oxidizing archaebacteria or nitrite oxidizing bacteria, iron reducing bacteria, sulfur reducing bacteria, anamox bacteria, and examples of the ammonia oxidizing bacteria may be mentioned *Nitrosomonas* genus, *Nitrosococcus* genus, *Nitrosospira* genus, etc., but are not limited thereto.

When the method for culturing microorganisms according to the present invention is employed, it is possible to effectively culture microorganisms even in difficult-to-be-cultured microorganisms, and it is possible to remarkably simplify the labor of centrifugation of the culture medium at the time of collecting microbial cells. In particular, when the method for culturing microorganisms according to the present invention is employed, hydroxylamine oxidoreductase (HAO) can be effectively produced.

The method for producing HAO of the present invention may include purifying HAO from a sample containing HAO and may include a step of measuring the activity of HAO to determine the fraction containing HAO in purification. In the step of measuring the activity of HAO, the method for measuring the activity of HAO of the present invention may be preferably applied, but the invention is not limited thereto.

The method for producing HAO of the present invention comprises, for example, the steps of culturing microorganisms by the method for culturing microorganisms of the present invention, crushing microbial cells of the microorganisms containing HAO, applying the supernatant fraction to a column, detecting the fraction containing HAO by using a method for measuring the activity of HAO, and if necessary, further applying it to a column under the condition of low oxygen concentration. The column used in the method for producing HAO of the present invention may be mentioned an anion exchange column, a gel filtration column, a hydroxyapatite column, a strong anion exchange column and a strong cation exchange column, etc., but the invention is not limited thereto. The production of HAO is preferably carried out under a condition of a low oxygen concentration, more preferably under a condition of an oxygen concentration of 0.5% or less.

The method for producing HAO of the present invention may contain a step of drying purified HAO for preservation.

EXAMPLES

Next, the present invention will be explained in more detail with reference to Examples, and the present invention is not limited to the following Examples unless it goes beyond its gist.

1. Production of HAO

Hydroxylamine oxidoreductase was produced. HAO was purified from ammonia oxidizing bacteria, and stored in a solution state or after drying, under a condition of low oxygen concentration.

1.1 Culture of Microorganisms 1.1.1 Strain

The following five kinds of ammonia-oxidizing bacteria were used.
Strain 1: *Nitrosomonas europaea* NBRC 14298 (purchased from NBRC[*1])

Strain 2: *Nitrosococcus oceani* ATCC 19707 (purchased from ATCC*² USA)
Strain 3: *Nitrosomonas* sp. NBRC 108559 (purchased from NBRC)
Strain 4: *Nitrosomonas cryotolerans* ATCC 49181 (purchased from ATCC)
Strain 5: *Nitrosospira multiformis* ATCC 25196 (purchased from ATCC)

*¹NBRC: National Institute of Technology and Evaluation, Biotechnology Center
*²ATCC: American type culture collection

1.1.2 Medium

The composition of the medium used was as follows.

1.1.2.1 Medium 1

Medium used for culturing
Strain 1: *Nitrosomonas europaea* NBRC14298
Strain 5: *Nitrosospira multiformis* ATCC25196

TABLE 1

| (per 1 liter) | |
| --- | --- |
| Ammonium sulfate [$(NH_4)_2SO_4$] | 2.5 g |
| HEPES [N-2-Hydroxyethyl piperazine-N'-2-ethane sulfonic acid] | 11.92 g |
| Potassium dihydrogen phosphate [$(KH_2PO_4)$] | 0.5 g |
| Sodium hydrogen carbonate [$NaHCO_3$] | 0.5 g |
| Magnesium sulfate heptahydrate [$MgSO_4 \cdot 7H_2O$] | 0.5 g |
| Calcium chloride dihydrate [$CaCl_2 \cdot 2H_2O$] | 100 mg |
| Ethylenediamine-N,N,N',N'-tetraacetate iron(III) sodium salt trihydrate [Fe(III)-EDTA] | 40 mg |
| Phenol red (pH indicator) | 0.01% w/v (final concentration) |
| Trace elements mixed solution (minute amount element solution) | 1 ml |

The pH was adjusted to 7.8 with an aqueous sodium hydroxide solution, and then autoclaved.

1.1.2.2 Medium 2 (Artificial Seawater Medium)

Medium used for culturing
Strain 2: *Nitrosococcus oceani* ATCC19707
Strain 4: *Nitrosomonas cryotolerans* ATCC49181

TABLE 2

| (per 1 liter) | |
| --- | --- |
| Ammonium sulfate [$(NH_4)_2SO_4$] | 2.5 g |
| HEPES [N-2-Hydroxyethyl piperazine-N'-2-ethane sulfonic acid] | 11.92 g |
| Sodium chloride [NaCl] | 27.5 g |
| Potassium chloride [KCl] | 0.72 g |
| Potassium dihydrogen phosphate [$KH_2PO_4$] | 15 mg |
| Sodium hydrogen carbonate [$NaHCO_3$] | 0.2 g |
| Magnesium sulfate heptahydrate [$MgSO_4 \cdot 7H_2O$] | 6.78 g |
| Magnesium chloride hexahydrate [$MgCl_2 \cdot 6H_2O$] | 5.38 g |
| Calcium chloride dihydrate [$CaCl_2 \cdot 2H_2O$] | 140 µg |
| Ethylenediamine-N,N,N',N'-tetraacetate iron(III) sodium salt trihydrate [Fe(III)-EDTA] | 5 mg |
| Phonol red (pH indicator) | 0.01% w/v (final concentration) |
| Trace elements mixed solution (minute amount element solution) | 1 ml |

The pH was adjusted to 7.8 with an aqueous sodium hydroxide solution, and then autoclaved.

1.1.2.3 Medium 3 (NBRC Medium 1201)

Medium used for culturing
Strain 3: *Nitrosomonas* sp. NBRC108559

TABLE 3

| (per 1 liter) | |
| --- | --- |
| Ammonium sulfate [$(NH_4)_2SO_4$] | 1 g |
| Dipotassium hydrogen phosphate [$K_2HPO_4$] | 0.5 g |
| Sodium hydrogen carbonate [$NaHCO_3$] | 0.5 g |
| HEPES [N-2-Hydroxyethyl piperazine-N'-2-ethane sulfonic acid] | 11.9 g |
| Magnesium sulfate heptahydrate [$MgSO_4 \cdot 7H_2O$] | 50 mg |
| Calcium chloride dihydrate [$CaCl_2 \cdot 2H_2O$] | 50 mg |
| Manganese(II) sulfide tetrahydrate [$MnSO_4 \cdot 4H_2O$] | 2 mg |
| Ethylenediamine-N,N,N',N'-tetraacetate iron(III) sodium salt trihydrate [Fe(III)-EDTA] | 5 mg |
| Sodium molybdate dihydrate [$Na_2MoO_4 \cdot 2H_2O$] | 50 µg |
| Cobalt(II) chloride hexahydrate [$CoCl_2 \cdot 6H_2O$] | 1 µg |
| Zinc sulfate heptahydrate [$ZnSO_4 \cdot 7H_2O$] | 0.1 mg |
| Phenol red (pH indicator) | 0.01% w/v (final concentration) |

The pH was adjusted to 7.8 with an aqueous sodium hydroxide solution, and then autoclaved.

1.1.2.4 Trace Elements Mixing Solution (Trace Elements Solution)

The following components were dissolved in 1 L of pure water.

TABLE 4

| Boric acid [$H_3BO_3$] | 30 mg |
| --- | --- |
| Manganese(II) chloride tetrahydrate [$MnCl_2 \cdot 4H_2O$] | 100 mg |
| Cobalt(II) chloride hexahydrate [$CoCl_2 \cdot 6H_2O$] | 190 mg |
| Nickel(II) chloride hexahydrate [$NiCl_2 \cdot 6H_2O$] | 24 mg |
| Copper(II) chloride dihydride [$CuCl_2 \cdot 2H_2O$] | 2 mg |
| Zinc sulfate heptahydrate [$ZnSO_4 \cdot 7H_2O$] | 144 mg |
| Sodium molybdate dihydrate [$Na_2MoO_4 \cdot 2H_2O$] | 36 mg |
| 25% Hydrochloric acid [25% HCl] | 12.5 ml |

1.1.3 Culture Method

The microorganisms were cultured in two ways, a normal culture method and a culture method using the dialysis tube according to the present invention. In the dialysis tube method, the microbial cells were suspended in 100 mL of medium, 50 mL thereof was taken from the suspension, the microbial cells were sealed in a 50-mL dialysis tube, and the tube was submerged in a 20 L medium and cultured. According to this method, although the culturing time becomes long, it is not necessary to recover the microbial cells by centrifugation of a large amount of culture medium.

1.1.3.1 Preculture

Each strain was cultured in a 50-mL plastic test tube (bioreactor tube, manufactured by TPP Ltd.) attached with a ventilation filter containing 30 mL of medium suitable for the strain. Since ammonia oxidizing bacteria secrete nitrous acid, the pH decreases with proliferation, and when the pH reaches around 6, it becomes a steady state and the growth stops. Therefore, the strain was cultured for about 1 week until phenol red which is a pH indicator contained in the medium became yellow (around pH 6.0).

1.1.3.2 Normal Culture Method Without Dialysis Tube

In a usual culture that does not use a dialysis tube, 30 mL of pre-cultured culture solution was charged in a 20-L plastic bottle (Nalgene clear boy, manufactured by Thermo Fisher Scientific Inc.) containing 20 L of a medium, and culture was carried. Culture was carried out in a room at room temperature of 26° C. by feeding air passed through an autoclaved vent filter (Millex-FG: manufactured by Millipore Corp.) by an air pump at 2.5 L/min. After one week, the pH indicator in the medium became yellow (pH 6.0), so the culture was terminated. The culture solution was transferred to a 500-mL plastic centrifuge tube, and centrifugation at 7,000 g was carried out a plurality of times to collect microbial cells. The collected microbial cells were charged in 50 mL of a plastic test tube after completely removing the medium, and after making the condition a low oxygen concentration by sealing a nitrogen gas, stored in a freezer at −80° C. until subjecting to purification method of the enzyme. An amount of microbial cells of each bacterium was about 1 to 2 g per 20 L of the medium.

1.1.3.3 Culturing Method Using Dialysis Tube

A small amount of pre-cultured bacteria was enclosed in a dialysis tube and then continuously cultured in a large bottle containing a large amount of medium. Specifically, it was carried out as follows.

The microbial cells in about 30 mL of pre-cultured medium were collected by centrifugation at 7,000 g, and resuspended in 50 mL of fresh medium. The resuspended microbial cells were charged in a dialysis tube (Spectra/Pore®6 Dialysis Membrane MWCO: 50 kDa: manufactured by SPECTRUM Lab.) which had been subjected to sterilization in an autoclave, and sealed with clip (manufactured by SPECTRUM Lab.) for a dialysis tube which had been subjected to sterilization in an autoclave. In addition, in order to prevent bacteria sticking to the vicinity of the enclosing port from proliferating in the external medium, the inlet was sterilized with ethanol for sterilization (available from Wako Pure Chemical Industries, Ltd.) and isodine scrub (available from Meiji Seika Pharma Co., Ltd.).

A dialysis tube filled with the microbial cells was charged in a 20-L plastic bottle (Nalgene clear boy, manufactured by Thermo Fisher Scientific Inc.) containing 20 L of a medium, and culture was carried. Culture was carried out in a room at room temperature of 26° C. by feeding air passed through an autoclaved vent filter (Millex-FG: manufactured by Millipore Corp.) by an air pump at 2.5 L/min. After three weeks, the pH indicator in the medium became yellow (pH 6.0), so the culture was terminated, and the culture solution containing the microbial cells was recovered from the dialysis tube. The culture solution was transferred to a 50-mL plastic centrifuge tube, and centrifugation at 7,000 g for 15 minutes was carried out to collect the microbial cells. After a nitrogen gas was sealed in the centrifuge tube containing the microbial cell pellets to make the condition a low oxygen concentration, the microbial cells were stored under frozen in a freezer at −80° C. until subjecting to purification method of the enzyme. An amount of microbial cells of each bacterium was about 1 to 2 g per 20 L of the medium.

By culturing using a dialysis tube mentioned above, it became possible to eliminate the trouble of collecting microbial cells from 20 L of culture which took longer than 6 hours, and to reduce the contamination risk of germs. Collecting microbial cells from about 50 mL of the medium in a dialysis tube was carried out by centrifuging at 7,000 g for 20 minutes using a 50-mL plastic centrifuge tube. In the case of culture using the dialysis tube, it was also possible to continue culturing by transferring to a fresh medium without collecting microbial cells. In addition, ammonia oxidizing bacteria which could easily be contaminated because of slow growth and easily floated so that difficult to collect microbial cells could be cultured and recovered remarkably efficiently by culturing using a dialysis tube.

1.2 Purification of HAO

1.2.1 Crushing and Collection of Supernatant Fractions

About 1 g of cryopreserved microbial cells in a plastic tube was thawed in running water and then suspended in 50 mL of buffer A (pH 7.5, 20 mM Tris-HCl buffer solution). The suspension was crushed with an ultrasonic crusher (UD-201, manufactured by TOMY Co., Ltd.) with OUTPUT 5.5 and DUTY 50 for 15 minutes. The cell lysate was centrifuged at 40,000 g for 30 minutes. A supernatant fraction containing HAO was recovered with 35 mL.

1.2.2 Purification of Anion Exchange Column

The supernatant fraction was added to three columns in which 5 mL of HiTrap Q HP (available from GE healthcare) had been connected in series and equilibrated with buffer A. Next, elution was carried out with a linear gradient with a sodium chloride concentration of 0 to 500 mM using buffer A and buffer B (pH 7.5, 20 mM of Tris-HCl buffer, 1 M of sodium chloride). Fractionation of the eluate was carried out with each 3 mL. A fraction containing HAO was detected and about 10 mL of the solution was recovered. Detection of the fraction containing HAO was carried out by the method described in 1.2.7 mentioned later.

1.2.3 Gel Filtration Column Purification

The recovered anion column eluted fraction was added to a gel filtration column HiLoad 26/600 Superdex 200 prep grade (available from GE healthcare) equilibrated with buffer B (pH 7.0, 20 mM of Tris-HCl buffer, 150 mM of sodium chloride). Next, buffer B was fed at 1.5 mL/min and eluted. Fractionation of the eluate was carried out with each 3 mL. The eluted fraction containing HAO was recovered with 12 mL.

1.2.4 Hydroxyapatite Column

The recovered eluted fraction from the gel filtration column was added to a column having an inner diameter of 1 cm, filled with 5 mL of CHT Ceramic Hydroxyapatite carrier (Type I, particle size 20 μm, available from BioRad) and equilibrated with buffer C (pH 7.5, 20 mM of potassium phosphate butter). Next, elution was carried out with a linear gradient with a potassium phosphate buffer of 20 to 500 mM using buffer C and buffer D (pH 7.5, 500 mM of potassium phosphate buffer). Fractionation of the eluate was carried out with each 2 mL. The eluted fraction containing HAO was recovered with 12 mL.

1.2.5 Strong Anion Exchange Column, or Strong Cation Exchange Column

The eluted fraction of the hydroxyapatite column was added to a strong anion exchange column of MonoQ 10/10 GL (available from GE healthcare) equilibrated with buffer A. Elution was carried out with a linear gradient with a sodium chloride concentration of 0 to 500 mM using buffer A and buffer B. Fractionation of the eluate was carried out with each 2 mL. Finally, a fraction containing HAO was recovered with 12 mL. Since only HAO derived from *Nitrosospira multiformis* was not adsorbed by MonoQ, a strong cation exchange column of MonoS 10/100 GL (available from GE healthcare) was utilized.

1.2.6 Devices for Purifying under Conditions of Low Oxygen Concentration without Inactivating Oxygen-Sensitive HAO HAO derived from bacteria other than *Nitrosomonas europaea* and Nitrosococcus oceani is extremely weak against oxygen, and most of part thereof is inactivated during purification which takes 2 to 3 days so that it was necessary to purify under the condition of low oxygen concentration. *Nitrosomonas europaea* and *Nitrosococcus oceani* are also expected to retain activity by purifying them under the condition of low oxygen concentration, so that they were also purified in the same way.

All buffers were deaerated by ventilating with nitrogen gas for 1 hour or more in advance to make the condition low oxygen concentration. The nitrogen gas used for ventilation showed a value of 0.00% of the detection limit by a low concentration oxygen monitor JKO-O2 Ver. 3 (manufactured by JIKCO Ltd.) (hereinafter referred to as oxygen concentration of 0.01% or less). The deaerated buffers were confirmed to be below the detection limit of 0.01 mg/mL or less by a dissolved oxygen meter (MultiLine Type 3410 optical DO electrode attached with type FD0925, manufactured by WTW GmbH).

During purification, a fraction collector of the chromatography system was covered with a plastic bag, and purification was carried out while keeping the condition of low oxygen concentration by constantly flowing nitrogen gas therethrough. The oxygen concentration in the plastic bag was 0.01% or less. In addition, nitrogen gas was also constantly fed into a glass bottle containing the deaerated buffer solution to prevent oxygen from dissolving therein and to maintain the condition of low oxygen concentration. When each chromatographic step was completed, samples were taken under the condition of low oxygen concentration while blowing nitrogen gas onto the fraction tube, and immediately shut down the lid.

1.2.7 Method for Judging Fractions Containing HAO in each Purification Step

For purification of HAO, AKTA Explore (available from GE healthcare) of chromatography system was used. Judgement of fractions containing HAO was carried out by measuring absorbance at three wavelengths by AKTA {280 nm (protein), 409 nm (heme), 463 nm (HAO specific heme P460)}, HAO fluorescence activity measurement by the resazurin method (phosphate citrate buffer with pH 5.6 was used), and band confirmation by SDS-PAGE was used in combination.

1.3 Storage Method of HAO

1.3.1 Storage by Solution (Short Term Storage)

It was stored in a 1.5-mL screw cap tube (manufactured by Fukae Kasei Co., Ltd.) attached with an 0-ring in a glove box with an oxygen concentration of 0.01% or less.

1.3.2 Storage by Drying (Long Term Storage)

5 nM of a HAO solution (buffer B) was spotted into each well of a 384-well microplate (available from Greiner bio-one) in an amount of each 0.1 μL, and air-dried at room temperature. After leaving at room temperature for about one day, when the activity was measured by the fluorescence method mentioned later, about 80% of the activity remained as compared with the case where before drying. After drying, when an aluminum sheet was stretched on a plate and stored at a low temperature, long-term storage was possible. All operations were carried out in a glove box under the condition of low oxygen concentration with an oxygen concentration of 0.01% or less.

2. HAO Fluorescence Activity Assay (Resazurin Method)

2.1 Reagent Preparation Method

Three kinds of stock solutions that can be stored for a long period of time were prepared for measurement.

2.1.1 Preparation of Stock Solution of Substrate (Hydroxylamine) for 4-Fold Dilution A 4 mM hydroxylamine hydrochloride solution (available from Tokyo Chemical Industry Co., Ltd.) was prepared using ultrapure water, and 10 mL each was dispensed into a 15-mL plastic tubes. At this time, the ultra-pure water was thoroughly deaerated beforehand and the operation was carried out in a glove box under the condition of low oxygen concentration (oxygen concentration of 0.01% or less). The prepared solution was cryopreserved at −80° C.

2.1.2 Preparation of Stock Solution of Tetrazolium Salt (Esazurin Salt) of Electron Acceptor for 4-Fold Dilution Similarly to the hydroxylamine mentioned above, 400 μM of a sodium resazurin solution (available from Wako Pure Chemical Industries, Ltd.) was prepared. The operation was carried out in a glove box under the condition of low oxygen concentration (oxygen concentration of 0.01% or less). The product was cryopreserved at −80° C.

2.1.3 Preparation of Stock Solution of Buffer for 2-Fold Dilution

A buffer (100 mM of potassium phosphate buffer and 300 mM of sodium chloride) for measurement was prepared. The operation was carried out in a glove box under the condition of low oxygen concentration (oxygen concentration of 0.01% or less). The solution already prepared was stored at 4° C. For the screening of HAO inhibitors, a buffer with a pH of 7.0 was prepared, and for confirmation of fractions containing HAO during purification of HAO and for measurement of HAO activity with direct soil, a buffer with a pH of 5.6 was prepared.

2.2 Implementing Method of Measuring Activity

Measurement was carried out by utilizing a 384-well microplate (MICROPLATE, 384 WELL, NON-BLINDING, F-BOTTOM, BLACK, available from Greiner Bio-One) and a dispenser mounted monochromator type microplate reader (infinite M1000 PRO: manufactured by Tecan Co.).

2.2.1 Mixing and Dispense of Stock Solution

A liquid amount was 100 μl per one assay and whole surface of 384 holes were used. For one-sheet of a plate, 38.4 mL of assay solution was required. First, 10 mL of a stock solution of a tetrazolium salt for 4-fold dilution, 20 mL of a stock solution of a buffer for 2-fold dilution, and 400 μl of a 5 μM HAO solution were slowly mixed. At this time, not only the HAO solution, but also HAO dried and stored on the plate can be utilized. The mixed solution was dispensed into each well of a 384-well microplate with each 75 μL using a 16-channel electric pipette (VIAFLO II 125 μL, available from INTEGRA Corp.).

2.2.2 Addition and Measurement of Substrate

A 384-well microplate in which reagents other than a substrate were dispensed was inserted into a plate reader. First, 25 μL of a hydroxylamine stock solution for 4-fold dilution as a substrate was each added to all wells by an injector equipped in a plate reader, and an amount of hydroxylamine to resazurin was adjusted to 10 times (molar ratio) in the reaction system. Thereafter, fluorescence measurement was immediately started (excitation wavelength 462 nm: wavelength width 20 nm, measurement wavelength 482 nm: wavelength width 20 nm). Measurements were carried out with a kinetic mode, all wells were measured once every minute, which was continued for 5 hours. The measurement was carried out at normal temperature. The measured value reached the maximum fluorescence intensity in about 2 hours. For comparison of the activity, it was possible to utilize an initial rate of enzyme activity, or activity value at the time less than 2 hours.

3. Application of Fluorescence Activity Assay

3.1 Application to HAO Inhibitor Screening

3.1.1 Investigation of Reagent Conditions

It was investigated to use the measurement of HAO fluorescence activity by the resazurin method for screening of HAO inhibitors. Specifically, the concentration of dimethyl sulfoxide (DMSO) frequently used as a solvent for the compound, and the concentration of the surfactant for preventing chemical aggregation, which causes nonspecific inhibition of the compound, were examined. In accordance with the activity assay mentioned above, it was examined by mixing these additives at the same time of mixing the stock solution. As a result, in 0.03% Triton-X 100 (surfactant) generally used, interfering effect of fluorescence measurement was not observed in particular. However, DMSO showed a remarkable decrease in fluorescence in proportion to its concentration, but if a DMSO concentration is about 0.5%, sufficient measurement (about half activity value compared with without DMSO) was found to be possible.

3.1.2 Preparation of Compound Library for Assay

To narrow down the candidate compounds for HAO inhibitors to be subjected to the screening experiment using the resazurin method, in silico screening was firstly carried out.

Based on the crystal structure of HAO derived from *Nitrosomonas europaea* and HAO derived from *Nitrosomonas oceani*, a pharmacophore search was conducted for a library of 5.3 million commercially available compounds (available from Namiki Shoji Co., Ltd.) using a drug development support software MOE (available from CCG Co.), and substrate mimic type compounds were searched. As a result, 1,000 hit compounds were obtained, and in fact 70 compounds were purchased. Among them, 40 compounds which were soluble in DMSO or water at a concentration of 100 mM were used as a compound library for screening.

3.1.3 Implementation of Screening

The HAO fluorescence activity measurement was carried out to the compound library for screening by the resazurin method, and the inhibitory effect of these compounds was verified. The 40 kinds of compounds were dissolved in DMSO for molecular biology (available from Wako Pure Chemical Industries, Ltd.) or ultrapure water at a concentration of 100 mM, and further 2-fold dilution series was prepared with 16 series (100 mM, 50 mM, 25 mM, 12.5 mM, 6.25 mM, 3.13 mM, 1.56 mM, 0.78 mM, 0.39 mM, 0.19 mM, 97 μM, 48.8 μM, 24.4 μM, 12.2 μM, 6.1 μM and 3.1 μM) (final concentration becomes 1/200 concentration thereof). As a positive control, a similar dilution series was also prepared for phenylhydrazine which is a known HAO inhibitor. 0.5 μL of the compound with each concentration was added to vacant wells of a 384-well microplate (MICROPLATE, 384 WELL, NON-BINDING, F-BOTTOM, BLACK, available from Greiner Bio-One) with a 16-channel electric pipette (12.5 μL of VIAFLO II, available from INTEGRA Corp.). A mixed solution of each stock solution of buffer, resazurin solution and HAO solution was prepared for 400 wells, and 75 μL per well for 384 wells was added with a 16-channel electric pipette (125 μL, of VIAFLO II, available from INTEGRA Corp.) (Composition per 1 well becomes 50 μL of buffer for 2-fold dilution, 25 μL of 400 μM resazurin for 4-fold dilution, and 0.5 μL of 5 nM HAO). The plate was inserted into a fluorescence plate reader attached with a reagent injector (infinite M1000 PRO, manufactured by Tecan Co.), and 25 μL of 4 mM hydroxylamine stock solution for 4-fold dilution was added per well, so that an amount of the hydroxylamine to that of the resazurin was made 10-fold amount (molar ratio) in the reaction system. After 2 hours of incubation, fluorescence measurement (excitation wavelength 562 nm: wavelength width 20 nm, measurement wavelength 592 nm: wavelength width 20 nm) was carried out. Candidate compound A was selected as a inhibitor which decreased the fluorescence intensity to 10% or less compared with without-inhibitor condition.

3.1.4 Determination of 50% Inhibitory Concentration of Candidate Compound A Determination of 50% inhibitory concentration of the candidate compound A obtained by screening against HAO was carried out by HAO fluorescence measurement according to the resazurin method. As an inhibitor for positive control, phenylhydrazine (available from Tokyo Chemical Industry Co., Ltd.) which is conventionally known as an irreversible inhibitor of HAO derived from *Nitrosomonas europaea* was used.

HAO derived from *Nitrosomonas europaea* was used. Phenylhydrazine and the candidate compound A were dissolved in DMSO at a concentration of 25 mM, and further 2-fold dilution series was prepared with 15 series (25 mM, 12.5 mM, 6.25 mM, 3.13 mM, 1.56 mM, 0.78 mM, 0.39 mM, 0.19 mM, 97 µM, 48.8 µM., 24.4 µM, 12.2 µM, 6.1 µM, 3.1 µM and 1.5 µM) (final concentration becomes 1/200 concentration thereof). These were spotted with 0.5 µL each in a 384-well microplate using a pipette. Each concentration was made n=4.

Next, measurements were carried out according to the above-mentioned conditions of 3.1.3. Nonlinear fitting was performed using Graph Pad Prism 6 (manufactured by GraphPad) to obtain 50% inhibitory concentration ($IC_{50}$). As a result, the $IC_{50}$ values for phenylhydrazine and the candidate compound A for HAO derived from *Nitrosomonas europaea* were found to be 276 nM and 43 nM, respectively.

3.1.5 Measurement of Inhibitory Effect of Candidate Compound A on Nitrification Activity of Ammonia Oxidizing Bacteria Verification of nitrification inhibitory effect (inhibitory action of nitrifying activity of ammonia oxidizing bacteria) of the candidate compound A was carried out using living bacteria of ammonia oxidizing bacteria (*Nitrosomonas europaea*). As an ammonia oxidizing bacteria, each bacterium was exchanged for a fresh medium of the same volume after mass culture (collected the bacteria when reaching around pH 6.0). The microbial cells were dispensed into a 384-well Deep well plate (available from BIO-BIK Co.) each with 100 µL. A dilution series solution (dissolved in DMSO) of each inhibitor was added in 0.5 µL (n=4 or 3). The mixture was stirred at 2,000 rpm for 1 minute. An air permeable plate seal (cell culture plate seal: AeraSeal) was stretched and incubated at normal temperature for 12 hours. After incubation, it was stirred at 2,000 rpm for 1 minute. The medium of 1 µL of each well was transferred to a 384-well microplate containing 50 µL of Greiss Reagent A solution. 50 µL of Greiss Reagent B solution was added to each well. After color development for 15 minutes, absorbance (545 nm) was measured with a plate reader. The 50% inhibitory concentration ($IC_{50}$) was calculated according to the manual in GraphPad Prism 6 software. The $IC_{50}$ of the candidate compound A was 1.8 µM. This experiment was referred to the literature of Greiss Reagent (Giustarini, D., Rossi, R., Milzani, A., & Dalle-Donne, I. (2008). Nitrite and nitrate measurement by Griess reagent in human plasma: evaluation of interferences and standardization. Methods in enzymology, 440, 361-80. doi:10.1016/S0076-6879 (07) 00823-3).

A: 2× Sulfanilamide Stock Solution

2% (w/w) sulfanilamide (available from Wako Pure Chemical Industries, Ltd.)

12% (v/v) phosphoric acid for biochemistry (available from Wako Pure Chemical Industries, Ltd.)

B: 2× NED Stock Solution 0.2% (w/w) N-(1-naphthyl)ethylenediamine (NED) (available from Wako Pure Chemical Industries, Ltd.)

Storage conditions: Both are placed in a light-shielding bottle and stored at 4° C.

3.2 Detection of Direct HAO Activity from Microorganism Community (a Soil, etc.) Containing Ammonia Oxidizing Bacteria A method for measuring HAO activity directly from a microorganism community such as a soil sample, etc., was found out. According to this method, it became possible to estimate the amount of the microbial cells and nitrification activity of the ammonia oxidizing bacteria in the soil.

0.5 g of a soil sample was placed in a 12-well plate (available from Corning, Inc.). 250 µL of potassium phosphate buffer for two-fold dilution with pH of 5.6 and 125 µL, of resazurin stock solution for 4-fold dilution were added. It was shaken and rotated at 300 rpm for 5 minutes. 125 µL of a hydroxylamine stock solution for 4-fold dilution was added, and an amount of the hydroxylamine to that of the resazurin was made 10-fold amount (molar ratio) in the reaction system.

At this time, autoclaved sterilized soil samples were used as a negative control. Further, in order to eliminate the resazurin reducing activity by an enzyme other than HAO, a well to which the candidate compound A of the HAO inhibitor obtained by the screening was added was prepared. The concentration of the inhibitor candidate A to be added was set to 100 µM which is sufficiently higher than the $IC_{50}$=1.8 µM for *Nitrosomonas europaea*.

The soil sample contains solid materials and suspended materials, and they shield or diffusely reflect the excitation light, whereby resulting in measurement noise. However, by covering the soil sample in the plate well with a mesh, it became possible to fix suspended materials to the bottom of the well without obstructing the water flow. Specifically, 0.5 g of the soil was placed in a well of a 12-well plate, and a net well (Netwell Insert 74 µm Polyester Mesh 15 mm Insert, 12 Well Plate: available from Corning, Inc.) of a cup attached with a mesh was fitted into each well from above. The net well was originally used for placing animal and plant tissues on the upper side of the mesh cup and carrying out culture of transplant and immunostaining, and it has never been known an example that was used to push solid materials during fluorescence measurement as in this method. Also, since the net well protruded about 5 mm on the plate, it could not be inserted into the plate reader (infinite M1000 PRO, manufactured by Tecan Co.) as it was. Thus, the top of the net well was cut with a heating wire cutter for foamed polystyrene, then it was fitted into the plate and inserted into the plate reader.

For the measurement, a plate reader (infinite M1000 PRO, manufactured by Tecan Co.) was used, and fluorescence measurement (excitation wavelength 562 nm: wavelength width 20 nm, measurement wavelength 592 nm: wavelength width 20 nm) was carried out in a kinetics mode every minute. During the time when the measurement was not carried out, incubation was carried out at room temperature (26° C.) by rotating and shaking at 150 rpm using a shake function of the plate reader.

At the incubation time of 60 minutes at which the fluorescence intensity became highest, the value derived from HAO present in the soil sample was determined from the difference in the relative fluorescence intensity between the untreated well and the inhibitor-added well.

3.3 Fluorescence Activity Staining of HAO

HAO activity in the gel was visualized by applying a solution of HAO fluorescence activity assay containing resazurin to a sample containing HAO subjected to native-PAGE which is nondenaturing polyacrylamide gel electrophoresis.

3.3.1 Preparation of Samples for Electrophoresis

As a sample of native-PAGE, the crushed supernatant of *N. europaea* prepared in the above item 1.2.1 was used. In addition, as a marker, purified HAO derived from *N. europaea* stored in the above item 1.3.1 was used. Each solution was mixed with sample buffer (0.4% bromophenol blue, 50% glycerol, pH 7.5, 5 mM Tris hydrochloride) with 1:1 and applied to native-PAGE.

3.3.2 Native-PAGE Electrophoresis

For native-PAGE electrophoresis, an e-PAGEL 15% polyacrylamide precast gel (available from ATTO Corp.) was used and was carried out according to the instruction manual. After setting the gel in the electrophoretic layer, 10 μL of the sample was each applied to the respective well in 2 lanes each. Gel electrophoresis was conducted at room temperature (about 25° C.) for 80 minutes at 300 V and 20 mA using an electrophoresis buffer for native-PAGE (25 mM Tris hydrochloride and 192 mM glycine).

3.3.3 Treatment of Gel with Buffer Containing Resazurin

After electrophoresis, the gel was subjected to shaking reaction in 30 mL of resazurin-containing buffer solution (a solution in which 10 mL of a resazurin solution for 4-fold dilution described in the item 2.1.2 mentioned above and 20 mL of a measurement buffer (pH 5.6) for 2-fold dilution described in the item 2.1.3 mentioned above are mixed) over 5 minutes to permeate the resazurin-containing buffer into the gel.

3.3.4 Visualization of Gel

Figure 5:
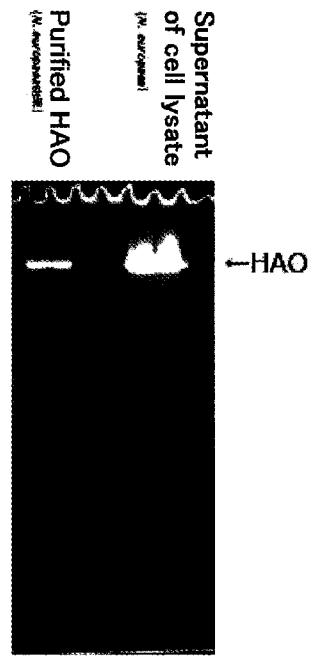
FIG. 5 shows a gel image obtained by subjecting a purified HAO of *N. europaea* and supernatant of sonicated microbial cells to nondenaturing polyacrylamide gel electrophoresis according to the present invention, and then, to fluorescence-active staining of HAO using resazurin. The band indicated by the arrow in the figure is HAO.

The gel was transferred from the buffer containing resazurin onto an acrylic tray and the excess solution was removed with a Kimwipe. 1 mL of the hydroxyl-amine solution of the substrate prepared in the item 2.1.1 mentioned above was uniformly applied to the gel, and after several seconds, the excess solution was removed with a Kimwipe. After reacting for about 30 seconds, fluorescent staining of the band was confirmed with a cyan color (wavelength 480-530 nm) gel imaging light source Cyanoview (available from ATTO Corp.) and an orange filter (available from ATTO Corp.), and photographed with a digital camera (FIG. 5). As a result, it was confirmed that there was one band fluorescing in the lane of the crushed supernatant of *N. europaea*. The position of this band was located at the same position as the band of purified HAO derived from *N. europaea* used as a marker, and it was confirmed to be a band of HAO. From the fluorescence intensity of the band, it was possible to conveniently quantify the HAO activity in the sample.

The invention claimed is:

1. A method for measuring activity of hydroxylamine oxidoreductase (HAO), the method comprising bringing a sample comprising HAO into contact with hydroxylamine in the presence of a resazurin salt, wherein the hydroxylamine is contacted with at a molar ratio of at least ten times of the resazurin salt, and the measurement is carried out at pH of 4.6 to 7.6, and measuring the activity of HAO in the sample by fluorescence measurement.

2. The measurement method according to claim 1, wherein the sample is selected from the group consisting of a soil, a compost, and an activated sludge.

3. A method for purifying HAO from a sample, the method comprising measuring activity of HAO in a sample by the method according to claim 1, and purifying HAO from said sample.

4. The producing method according to claim 3, wherein the method further comprises drying the purified HAO.

5. The measurement method according to claim 1, wherein the sample is a polyacrylamide gel obtained by electrophoresing one selected from the group consisting of a soil, a compost, and an activated sludge in a nondenaturing state.

* * * * *